United States Patent
Wade

(10) Patent No.: US 12,011,143 B2
(45) Date of Patent: *Jun. 18, 2024

(54) ENHANCED VIDEO ENABLED SOFTWARE TOOLS FOR MEDICAL ENVIRONMENTS

(71) Applicant: Jack Wade, La Jolla, CA (US)

(72) Inventor: Jack Wade, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/844,641

(22) Filed: Jun. 20, 2022

(65) Prior Publication Data

US 2023/0019411 A1    Jan. 19, 2023

Related U.S. Application Data

(63) Continuation of application No. 16/942,477, filed on Jul. 29, 2020, now Pat. No. 11,376,094, which is a
(Continued)

(51) Int. Cl.
*G06F 3/0481* (2022.01)
*A61B 1/00* (2006.01)
(Continued)

(52) U.S. Cl.
CPC .. *A61B 1/000094* (2022.02); *A61B 1/000095* (2022.02); *A61B 1/00011* (2013.01);
(Continued)

(58) Field of Classification Search
CPC ....... G06T 2200/24; G06T 2207/30004; G06F 3/0481; G06F 18/2413; G06F 18/214; A61B 1/3132; A61B 34/25; A61B 90/361; A61B 1/000094; A61B 1/00011; A61B 1/000095; A61B 1/00009; G06K 19/06028; G06K 19/06037; G16H 10/60; G16H 50/20; G16H 50/30; G16H 15/00; G16H 40/63; G16H 40/20; G16H 50/70;
(Continued)

(56) References Cited

U.S. PATENT DOCUMENTS

| | | | |
|---|---|---|---|
| 2003/0159141 A1* | 8/2003 | Zacharias | H04N 5/445 348/E5.093 |
| 2005/0024724 A1* | 2/2005 | Kim | G06T 15/08 359/462 |

(Continued)

*Primary Examiner* — Rayeez R Chowdhury
(74) *Attorney, Agent, or Firm* — Olivo IP Law Group, P.C.; John W. Olivo, Jr.

(57) ABSTRACT

Medical software tools platform utilizes a surgical display to provide access to specific medical software tools, such as medically-oriented applications or widgets, that can assist those in the operating room, such as a surgeon or surgical team, with a surgery. For various embodiments, the medical software tools platform and its associated medical software tools are presented on a surgical display (e.g., being utilized in an operating room) over an image stream provided by a surgical camera (e.g., in use in the operating room or with other endoscopic procedures). Various medical software tools can provide features and functions that can facilitate integration of equipment in an operating room or add medical context awareness to anatomic structures presented in the image stream from the surgical camera and provide archived information pertaining to the same.

11 Claims, 13 Drawing Sheets

Related U.S. Application Data continuation of application No. 15/456,458, filed on Mar. 10, 2017, now Pat. No. 10,758,314, which is a continuation-in-part of application No. 15/377,817, filed on Dec. 13, 2016, now abandoned, which is a continuation of application No. 14/107,329, filed on Dec. 16, 2013, now Pat. No. 9,526,586.

(60) Provisional application No. 61/865,037, filed on Aug. 12, 2013.

(51) Int. Cl.
  *A61B 1/313* (2006.01)
  *A61B 34/00* (2016.01)
  *A61B 90/00* (2016.01)
  *H04L 67/125* (2022.01)

(52) U.S. Cl.
  CPC ............ *A61B 1/3132* (2013.01); *A61B 34/25* (2016.02); *A61B 90/361* (2016.02); *G06F 3/0481* (2013.01); *G06T 2200/24* (2013.01); *G06T 2207/30004* (2013.01); *H04L 67/125* (2013.01)

(58) Field of Classification Search
  CPC ........ G16H 30/40; G16H 40/67; G16H 50/50; G16H 20/17; G16H 30/20; G16H 80/00; G16H 10/20; G16H 20/90; G16H 70/00; G16H 20/40; G16H 70/20; G16H 10/65; G16H 20/10; G16H 40/40; G16H 40/60
  See application file for complete search history.

(56) References Cited

U.S. PATENT DOCUMENTS

| | | | | |
|---|---|---|---|---|
| 2008/0304724 | A1* | 12/2008 | Eino | A61B 1/00022 382/128 |
| 2009/0036902 | A1* | 2/2009 | DiMaio | A61B 8/12 606/130 |
| 2010/0081930 | A1* | 4/2010 | Dunbar | A61B 8/465 600/437 |
| 2011/0141140 | A1* | 6/2011 | Duhamel | A61B 1/317 345/629 |
| 2015/0126859 | A1* | 5/2015 | Popovic | A61B 90/39 600/426 |

* cited by examiner

ENHANCED VIDEO ENABLED SOFTWARE TOOLS FOR MEDICAL ENVIRONMENTS

PRIORITY CLAIMS

This application is a continuation of U.S. patent application Ser. No. 16/942,477, filed Jul. 29, 2020, which is a continuation of U.S. patent application Ser. No. 15/456,458, filed on Mar. 10, 2017, which is a continuation in part of U.S. patent application Ser. No. 15/377,817, filed Dec. 13, 2016, which is a continuation of U.S. patent application Ser. No. 14/107,329, filed Dec. 16, 2013, and issued as U.S. Pat. No. 9,526,586 on Dec. 27, 2016, which claims the benefit of U.S. Provisional Patent Application Ser. No. 61/865,037, filed Aug. 12, 2013, entitled "TOOLS PLATFORM FOR MEDICAL ENVIRONMENTS", which is incorporated herein by reference.

TECHNICAL FIELD

The technology disclosed herein relates to medical software tools and, in particular, some embodiments relate to systems and methods for a software tools platform in a medical environment, such as a surgical environment.

BACKGROUND OF THE INVENTION

During minimally invasive surgeries, medical imaging devices may be introduced into a subject's body to illuminate and image body cavities, organs or other tissue. Advantages of using internal medical imaging devices include the ability to avoid large incisions and the ability to image biological tissue. Many imaging devices also include one or more lenses that focus images onto an eyepiece and/or imaging lens. Still or video cameras may be used to capture image data using a medical imaging device.

Medical imaging devices can enable surgeries to be performed in a manner that is less intrusive and often safer for patients. While this brings many benefits to patients, it presents a number of challenges for the surgeon who must work within a very confined surgical compartment. In particular, surgeons must deal with poor visibility, limited lighting, and a narrow viewing angle. Because of their size, conventional medical imaging devices tend to have limited imaging resolution, often fail to provide more than one perspective of biological tissue, and due to visible lighting constraints, often fail to show differences in biological tissue.

Minimally invasive surgeries increasingly occur in operating rooms equipped with advanced audio visual technology. At one end of the spectrum are integrated operating rooms, that combine high resolution video displays, touch screen control, access to digital information through the hospital network, and data archiving capability into an interconnected purpose-built system. In addition to facilitating surgical procedures and improving efficiency, integrated operating rooms can also connect the surgeon in the sterile field with people and information outside the operating room. For example, an integrated operating room can enable: live consultation with pathology and ICU; real-time collaboration with surgeons across the globe; live feeds to conference rooms and auditoriums for training and grand rounds; and data exchange with an electronic medical record system, radiological picture archiving and communication system (PACS), or network-enabled devices in other operating and treatment rooms.

SUMMARY OF THE INVENTION

Various embodiments of the disclosed technology provide a medical software tools platform that utilizes a surgical display to provide access to medical software tools, such as medically-oriented applications or widgets, that can assist those in the operating room, such as a surgeon and their surgical team, with a surgery. For various embodiments, the medical software tools platform and its associated medical software tools are presented on a surgical display (e.g., being utilized in an operating room) over an image stream provided by a surgical camera (e.g., in use in the operating room) or other medical device that generates image streams. An image stream can include video or a series of static images (e.g., medical ultrasound device). Various medical software tools can provide features and functions that can facilitate integration of equipment in an operating room or add medical context awareness to anatomic structures presented in the image stream from the surgical camera.

In some contexts, visual data streams to a single large panel video display or a multi-screen display configuration are provided by two or more computer systems, each being controlled by a computer operator (i.e., user) using such input/output (I/O) devices as keyboards, mice, and as video monitor. At times, it is convenient for the computer operator to share the IO devices between the computers by means of a device that switches the IO devices between the multiple computers. These switches, often referred to as a Keyboard-Video-Mouse (KVM) switch, are commanded by the computer operator (e.g., commanded by a special keyboard sequence or a button on the KVM switch) to switch a common keyboard, mouse, or video monitor between controlling the computer systems.

According to some embodiments, a system comprises an image stream interface module configured to receive an image stream from a surgical camera, a user interface overlay module configured to provide a user interface overlay adapted for presentation over the image stream, and a medical software tools module configured to provide a medical software tool through the user interface overlay. The medical software tool may be configured to perform an operation with respect to the image stream and provide an output adapted to be presented over the image stream. The user interface overlay can include a graphical user interface (GUI) that permits visibility of at least some of the image stream underlying the user interface overlay. The user interface overlay module is further configured to present the output over the image stream. Depending on the embodiment, the surgical camera may be an endoscope or a laparoscope. Additionally, the image stream interface module may receive the image stream from the surgical camera through an image stream processing system.

Throughout this description, a user interface will be understood to be accessible to any user involved in a medical procedure, such as a surgery. It will also be understood that a user can include any individual involved in a given medical procedure, such as a nurse or a surgeon.

In some embodiments, the system comprises a medical device communication module configured to exchange data between a medical device and the medical software tool. Through the medical device interface module, some embodiments can enable a medical software tool to present information from disparate medical devices, or facilitate sharing of information between medical devices. In some embodiments, the system comprises an image stream processing system interface module configured to exchange data between an image stream processing system and the medical software tool, the medical software tool being configured to modify a setting of the image stream processing system. The setting of the image stream processing system can include enabling or disabling application of an image stream processing algorithm to the image stream. Through the image stream processing system interface module, the medical software tool can control how the image stream processing system receives and processes image streams eventually presented on the surgical display.

Depending on the embodiment, the operation performed by the medical software tool may comprise a visual tag over the image stream in association with an anatomical structure or tissue presented in the image stream, and the output may comprise the visual tag. The operation performed by the medical software tool may comprise measuring an anatomical structure or tissue (e.g., width, height, length, or volume) presented in the image stream, and the output may comprise a resulting measurement. Where the image stream comprises two-dimensional content, the operation may comprise converting at least some of the two-dimensional content into three-dimensional content, and the output may comprise the three-dimensional content (e.g., stereoscopic three-dimensional content). The operation performed by the medical software tool may comprise associating content in the image stream with a timer, and the output may comprise a visual representation of the timer. The operation performed by the medical software tool may comprise identifying content (e.g., anatomic structure) in the image stream similar to reference content (e.g., reference anatomic structure), and the output may comprise a visual indication of the identified content.

According to some embodiments, a computer program product comprises code configured to cause a computer system to perform various operations described herein. Additionally, some embodiments may be implemented using a computer system as described herein. Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

A system or method in accordance with the present invention may selectively and dynamically route one or more image input streams through one or more dynamically selectable and iterative algorithm processing elements (or modules) before the resulting processed streams are routed to one or more selectable outputs. For some embodiments, dynamic selection with respect to inputs means that one or more inputs can be selected or unselected in real time for routing to one or more image processing elements. For additional embodiments, dynamic and iterative selection with respect to processing elements means that a selected image stream can be routed to one or more image processing elements simultaneously and in real time. The routing may be based upon criteria relating to the image stream's source, the image stream's content, or on the processing results of a preceding image processing element. The output of an image processing element may be directed back to the system or method for routing to a subsequent image processing element, or to one or more image outputs that supply an image stream to an output device (e.g., display, image recorder, or other image processor, or transmission device).

An exemplary system for collaboratively switching an image stream input to an image stream output, comprising: an image stream input interface; an image stream output interface; a first image processing module, wherein the first image processing module is configured to accept an image stream from the image stream input interface or another image processing module, apply an image processing function to the image stream, and output a processed image stream; and a switching matrix, wherein the switching matrix is in communication with the image stream input interface, the image stream output interface, and the first image processing module such that the switching matrix can selectively map (i.e., route) the image stream input interface to the image stream output interface or to the first image processing module, and the switching matrix can selectively map the processed image stream from the first image processing module to the image stream output interface or to a second image processing module. An image stream includes both a steady flow of image frames (i.e., video) and image stills captured at a set interval (e.g., once every hour). Additionally, for some embodiments the system comprises a plurality of image processing modules, a plurality of image stream input interfaces, or a plurality of image stream output interfaces. Furthermore, in further embodiments, the system may be integrated into a display having a display output, wherein the image stream output interface is in communication with the display output.

In some embodiments, the image processing module is a field programmable gate array (FPGA) to which algorithms, such as image processing functions, can be programmed and changed if desired. Additionally, with the use of multiple images processing functions, algorithms, such as image processing functions, can be executed in a predetermined or adaptive sequence. Exemplary algorithms include convolutions, real-time adaptive histograms, and algorithms capable of processing multiple frames simultaneously (e.g., image subtraction function).

One of ordinary skill in the art would understand that, depending on the embodiment, either the image stream input interface, the image stream output interface, or both may utilize unidirectional communication or bidirectional communication with input devices and output devices. For example, a system may be configured to receive control information from a controller interface device via an image stream output interface, or to send control information to an image source via an image stream input interface. In another example, the control information is received by the system through the Display Data Channel (DDC). Depending on the embodiment, the system may be configured to send control information to a device external to the system, through the image stream input interface.

In some embodiments, the switching matrix may selectively map an image stream input interface or a processed image stream in real-time. In further embodiments, the switching matrix may selectively map the image stream input interface to more than one image processing module or to more than one image stream output interface simultaneously. Additionally, in some embodiments, the switching matrix may selectively map the processed image stream to more than one image processing module or to more than one image stream output interface simultaneously. In other embodiments, the switching matrix may selectively map an image stream input interface or the processed image stream based on a criterion. For example, the switching matrix may selectively map an image stream input interface or a processed image stream based on its source or content. In another example, the switching matrix may selectively map a processed image stream based on the results of a preceding image processing module. Depending on the embodiment, the image processing module may have the capability of processing a plurality of image streams in parallel. The image stream interface for some embodiments may be configured to receive the image stream from an image stream capture device, an image stream playback device, a computer system, a sensor device (e.g., sensors typically found on an aircraft, such as a radar system), or a medical device (e.g., endoscope). The image stream output interface for some embodiments may be configured to output to a display (e.g., liquid crystal display monitor), a computer system, or recording device (e.g., digital video recorder). Further, in some embodiments, the system may be configured to output an image stream through a virtual display.

In numerous embodiments, the system further comprises a data input interface, wherein the switching matrix is further in communication with the data input interface such that the switching matrix can further selectively map the data input interface to the image stream output interface or to the first image processing module. For some such embodiments, the image stream input interface may comprise the data input interface.

With respect to protocols and interface types, in various embodiments, the image stream input interface or image stream output interface has a Digital Video Interface (DVI) connector, High-definition Multimedia Interface (HDMI) connector, a Bayonet Neill-Concelman (BNC) connector, a fiber optic connector, a DisplayPort connector, a Universal Serial Bus (USB) connector, or a Firewire (IEEE1394) connector. In regard to formats, the image stream input interface is configured to convert from or the image stream output interface is configured to: a Digital Video Interface (DVI) standard (e.g., DVI-D digital mode, DVI-A analog mode), a High-definition Multimedia Interface (HDMI) compatible standard, a Red-Green-Blue (RGB) Analog standard, a Red-Green-Blue (RGB) Digital standard, a DisplayPort standard, a National Television System Committee (NTSC) standard, a Phase Alternate Line (PAL) standard, or a Serial Digital Interface (SDI) standard.

The image processing function in some embodiments may comprise an image stream mix function, an image stream scale function, an image stream blend function, an image stream encoding algorithm, or an image stream enhancement function. For those embodiments having an image stream enhancement function, the image stream enhancement function may comprise a de-haze function, a de-blur function, a shadow function, a dawn-dusk function, a fusion function, a (motion) stabilization function, a thermal turbulence function, an equalization function, an edge detection function, a rain and fog function, or a light optimizing function. Further, in some embodiments, the system can eliminate or reduce frame latency by configuring an image processing module to apply processing results of a given frame to a subsequent frame.

In additional embodiments, where the image stream is provided by an endoscope, the image processing function can enhance the image stream for detecting texture differences in living tissue, detecting a polyp, detecting anomalous tissue, detect blood circulation, or identifying reference locations for subsequent registration of images from another modality. In further embodiments, a light optimizing function may adjust a color channel for the image stream in order to detect polyps. For example, the system may apply image processing functions in real time to image feeds from an endoscope in order to detect differences in living tissue, detect anomalous tissue, determine boundaries where tissue texture changes (for tissue volume and size information), and identify reference locations for subsequent registration of images from other modalities.

With respect to the last objective for image processing function, image registration is the process of determining the alignment between two images that have overlapping regions, where the images may be acquired at different times and/or by different sensors. The difficulty in aligning such images is further increased during multi-modal image registration, where the images are acquired using different imaging techniques (e.g., two images that share similar content may have very different intensity mappings).

These and other features, embodiments, and aspects of the present invention can be appreciated from the following drawing description and detailed description of a preferred embodiment.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION OF THE PREFERRED EMBODIMENT

Figure 1:
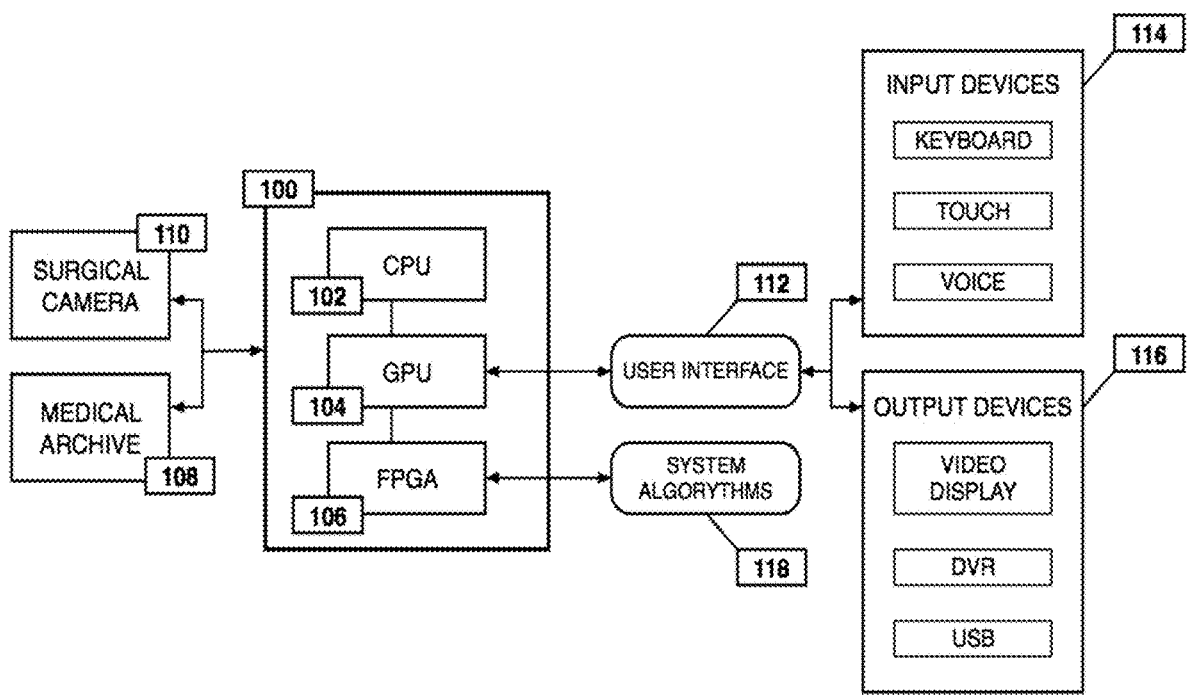
FIG. 1 is a block diagram illustrating an example of the overall processing system that may be used in implementing various features of embodiments of the disclosed technology.

FIG. 1 is a block diagram illustrating an example of the overall processing system that may be used in implementing various features of embodiments of the disclosed technology. In accordance with the preferred embodiment of the present invention, the processing system 100 consists of processor elements such as: a central processing unit (CPU) 102; a graphics processing unit (GPU) 104; and a field programmable gate array (FPGA) 106. The processing system 100 may be used to retrieve and process raw data derived from a surgical camera or a data storage device, such as a medical archive 108. The surgical camera 110 or medical archive 108 transmits a data stream to the processing system 100, whereby that data is processed by the CPU 102. The FPGA 106, connected to the CPU 102 and the GPU 104, simultaneously processes the received data by using a series of programmed system algorithms 118, thus functioning as an image clarifier within the processing system 100. The GPU 104 communicates with the user interface 112 to display the received data from the medical archive 108. The GPU 104 enables the user interface to then communicate the data to connected input devices 114 and output devices 116. The user interface 112 can communicate to multiple input 114 and output devices 116 simultaneously. An input device 114 can include, for example, a keyboard, touchscreen or voice activated device. An output device 116 can include, for example, a video display, a digital video recorder (DVR) or universal serial bus (USB).

Figure 2:
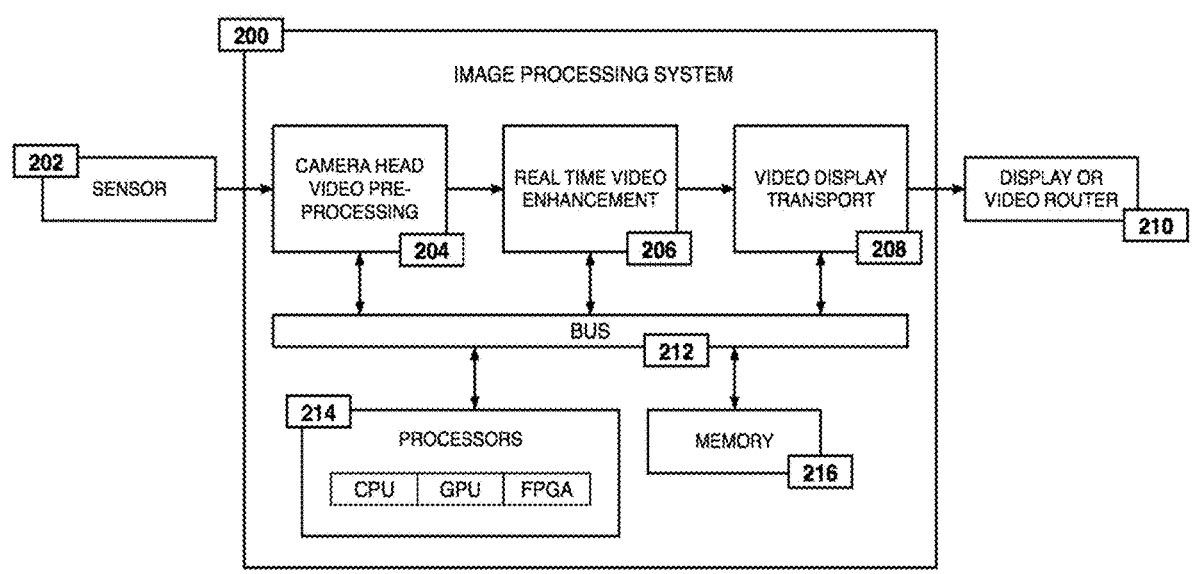
FIG. 2 is a block diagram illustrating an example of the image processing system that may be used in implementing various features of embodiments of the disclosed technology.

FIG. 2 is a block diagram illustrating an example of the image processing system that may be used in implementing various features of embodiments of the disclosed technology. In accordance with the preferred embodiment of the present invention, the image processing system 200 consists of three components that process image data received from a sensor 202 in order to send that data to a display or video router 210. The three components of the image processing system 200 are: camera head video pre-processing 204; real time video enhancement 206; and the video display transport 208 function. Image data is collected by a sensor imaging device 202, and is then transmitted to the camera head video pre-processing component 204 within the image processing system 200. This data may be, for example, a raw video image that is pre-processed using various image processing algorithms. Image pre-processing may also include software modules for image registration and segmentation to optimize the video data and communicate via the system bus 212 with the internal system processors 214: the CPU; GPU; and FPGA.

The pre-processed image data is transmitted to the real time video enhancement 206 component, whereby the image data is enhanced to improve clarity or highlight certain details. Once the image data resolution has been enhanced, the video display transport 208 component completes image post-processing, formatting from the initial sensor resolution to the eventual display resolution, for example, enhancing the video data to 1080p HD or 4K display resolution or using software modules such as video cross conversion, scaling and adding graphic overlays. The processed image data is then transmitted from the image processing system 200 to the display or video router 210. The video display transport also saves the processed image data to the processing system memory 216 that can consist of internal and external memory storage.

Figure 3:
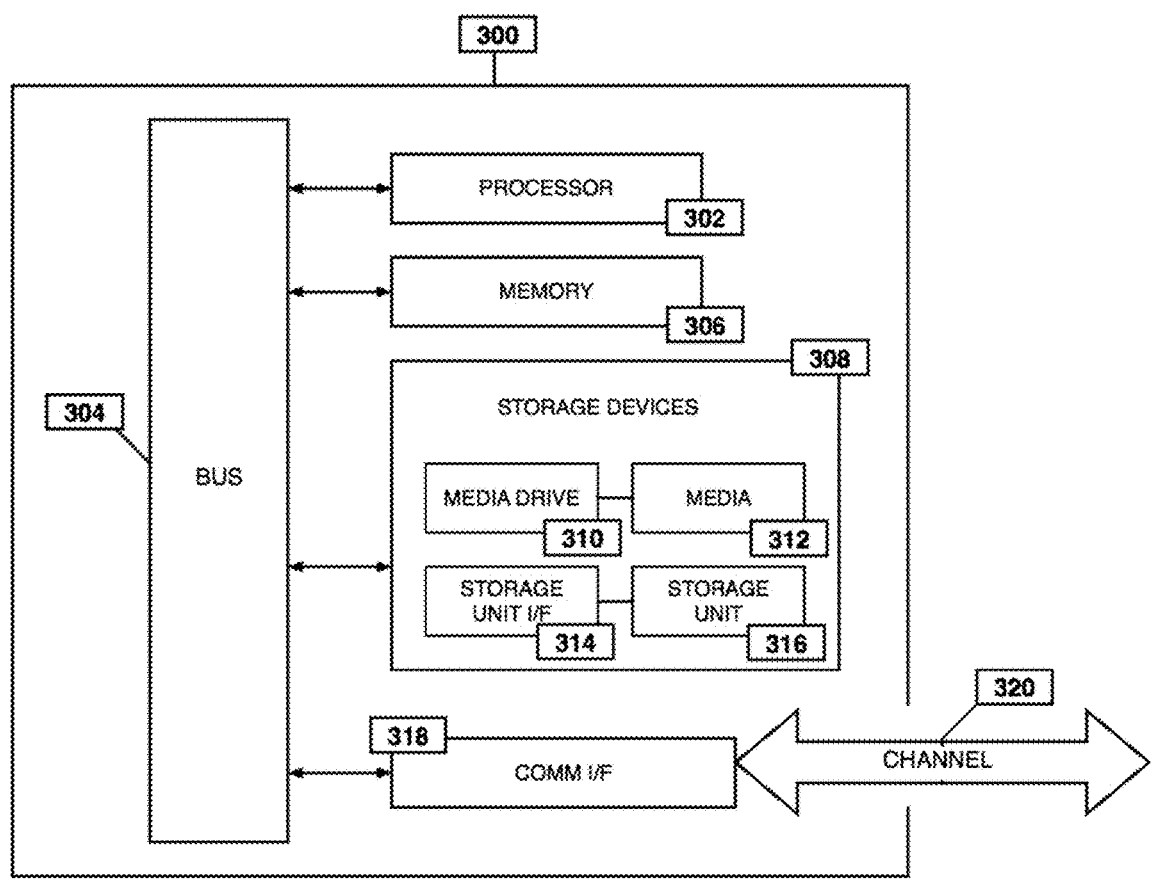
FIG. 3 illustrates an example computing module that may be used in implementing various features of embodiments of the disclosed technology.

FIG. 3 illustrates an example computing module that may be used in implementing various features of embodiments of the disclosed technology. Where components or modules of the technology are implemented in whole or in part using software, in one embodiment, these software elements can be implemented to operate with a computing or processing module capable of carrying out the functionality described with respect thereto. One such example computing module 300 is shown in FIG. 3. Various embodiments are described in terms of this example computing module 300.

The computing module 300 may represent, for example, computing or processing capabilities found within desktop, laptop and notebook computers; hand-held computing devices (PDA's, smart phones, cell phones, palmtops, etc.); mainframes, supercomputers, work stations or servers; or any other type of special-purpose or general-purpose computing devices as may be desirable or appropriate for a given application or environment. The computing module 300 might also represent computing capabilities embedded within or otherwise available to a given device. For example, a computing module 300 might be found in other electronic devices such as, for example, digital cameras, navigation systems, cellular telephones, portable computing systems, modems, routers, WAPs, terminals and other electronic devices that might include some form of processing capability.

The Computing module 300 might include, for example, one or more processors, controllers, control modules, or other processing devices, such as a processor 302. The processor 302 might be implemented using a general purpose or special purpose processing engine, including but not limited to: a microprocessor; controller; or other control logic. In the computing module 300, the processor 302 is connected to a bus 304, although any communication medium can be used to facilitate interaction with other components of computing module or to communicate externally.

The computing module 300 might also include one or more memory modules, simply referred to herein as main memory 306. For example, preferably random access memory (RAM) or other dynamic memory might be used for storing information and instructions to be executed by processor. Main memory 306 might also be used for storing temporary variables or other intermediate information during execution of instructions to be executed by processor. The computing module 300 might likewise include a read only memory ("ROM") or other static storage device coupled to bus for storing static information and instructions for the processor 302.

The computing module 300 might also include one or more various forms of information storage mechanism 308, which might include, for example, a media drive 310, and a storage unit interface 314. The media drive 310 might include a drive or other mechanism to support fixed or removable storage media 312. For example, a hard disk drive, a floppy disk drive, a magnetic tape drive, an optical disk drive, a CD or DVD drive (R or RW), or other removable or fixed media drive might be provided. Accordingly, storage media 312 might include, for example, a hard disk, a floppy disk, magnetic tape, cartridge, optical disk, a CD or DVD, or other fixed or removable medium that is read by, written to, or accessed by media drive 310. The storage media 312 can include a computer usable storage medium having stored therein computer software or data.

In alternative embodiments, information storage mechanism 308 might include other similar instrumentalities for allowing computer programs or other instructions or data to be loaded into computing module 300. Such instrumentalities might include, for example, a fixed or removable storage unit 316 and an interface 314. Examples of such storage units 316 and interfaces 314 can include a program cartridge and cartridge interface, a removable memory (for example, a flash memory or other removable memory module) and memory slot, a PCMCIA slot and card, and other fixed or removable storage units 316 and interfaces 314 that allow software and data to be transferred from the storage unit 316 to the computing module 300.

The computing module 300 might also include a communications interface 318 that might be used to allow software and data to be transferred between computing module 300 and external devices. Examples of a communications interface 318 might include a modem or soft modem, a network interface (such as an Ethernet, network interface card, WiMedia, IEEE 802.XX or other interface), a communications port (such as for example, a USB port, IR port, RS232 port Bluetooth® interface, or other port), or other communications interface 318. Software and data transferred via a communications interface 318 might typically be carried on signals, which can be electronic, electromagnetic (which includes optical) or other signals capable of being exchanged by a given communications interface 318. These signals might be provided to communications interface via a channel 320. This channel 320 might carry signals and might be implemented using a wired or wireless communication medium. Some examples of a channel 320 might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 306, storage unit 316, media 312, and channel 320. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 300 to perform features or functions of the disclosed technology as discussed herein.

Figure 4:
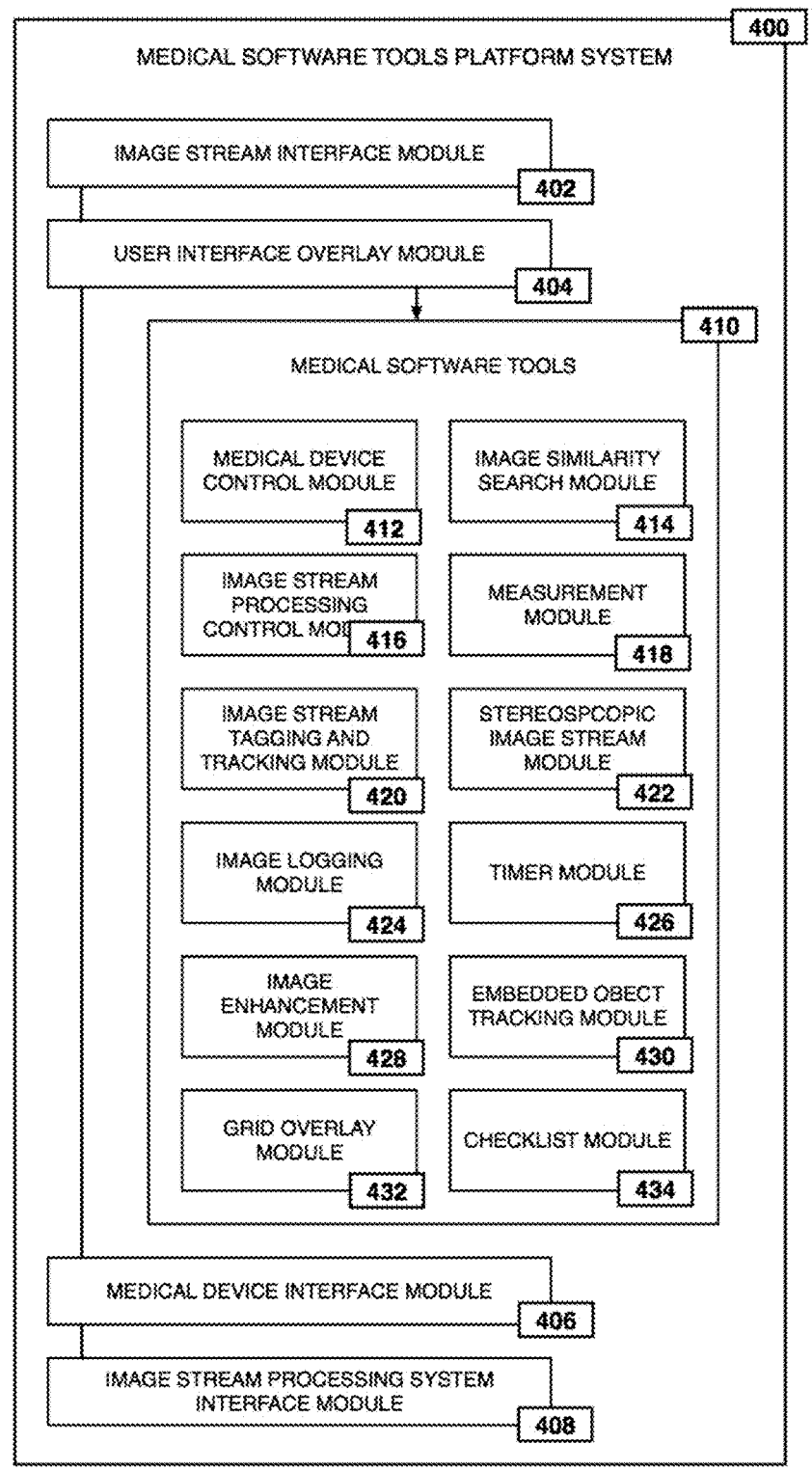
FIG. 4 is a block diagram illustrating an example medical software tools platform in accordance with some embodiments of the technology described herein.

FIG. 4 is a block diagram illustrating an example medical software tools platform system in accordance with some embodiments of the technology described herein. The medical software tools platform provides access to medically-oriented applications (apps) or widgets that can assist members of the surgical team during an operation. For example, during a surgery it is common to clamp a blood vessel for a short period, but the clamp must be removed before damage occurs to the tissue that depends on the vessel's blood flow for necessary oxygenation. A timer app could be used to apprise the surgeon of the elapsed time and also the remaining time that it is safe for the clamp to be in place. Additionally, the timer app could monitor the area around the clamped blood vessel for changes in color which would indicate declining levels of tissue oxygenation and generate an alert when the color indicates tissue oxygen saturation may be declining below safe levels. In a second example, a grid overlay app could overlay gridlines over a portion of the displayed video stream. The gridlines provide a means of marking the location of biopsy samples. Additionally, the gridlines allow the surgeon to accurately measure anatomical structures that are displayed. As a third example, an annotation tool app allows the surgeon to superimpose circles or squares or to draw around features or areas of interest displayed on the screen and associate digital tags or notes for future reference. In a final example, when surgeons excise diseased tissue it is common to also remove a narrow margin around it. The challenge, of course, is to clearly visualize and identify the demarcation between diseased and healthy tissue. A boundary tool app could identify anomalous areas of tissue using texture analysis techniques to assist the surgeon in finding diseased areas and demarcating them. Such a tool could potentially also be useful in helping a surgeon identify the best locations for obtaining biopsy samples.

In accordance with the preferred embodiment of the present invention, The medical software tools platform system 400 includes: an image stream interface module 408; a user interface overlay module 404; medical software tools 410; a medical device interface module 406; and an image stream processing system interface module 408. The medical software tools platform system 400 may be integrated, in whole or in part, into a video display or an image stream processing system utilized in an operating room. The image stream interface module 402 may receive an image stream acquired by a surgical camera or the like. Depending on the embodiment, the image stream may be received directly from the surgical camera, or may be provided by way of one or more components, such as an image stream processing system. The image stream received from the image stream interface module 402 may vary in resolution, frame rate, format, and protocol according to the surgical camera or the image stream processing system providing the image stream.

The user interface overlay module 404 may provide a user interface to the medical software tools platform system 400, which may include one or more graphical user interface (GUI) elements presented over the image stream received through the image stream interface module 402. For some embodiments, the user interface comprises a bottom toolbar configured to be presented over the image stream, and configured to provide access to various medical software tools 410 available through the medical software tools platform system 400.

The medical software tools 400 may include one or more medical software tools, such as medically-oriented applications or widgets, which can be utilized with respect to the image stream being received through the image stream interface module 402. The medical software tools 410 platform includes but is not limited to: a medical device control module 412; an image similarity search module 414; an image stream processing control module 416; a measurement module 418; an image stream tagging and tracking module 420; a stereoscopic image stream module 422; an image logging module 424; a timer module 426; an image enhancement module 428; an embedded object tracking module 430; a grid overlay module 432; and a checklist module 434.

The medical device interface module 406 may facilitate communication between the medical software tools platform system 400, one or more of the medical software tools 410, and one or more various medical devices utilized in an operating room. The image stream processing system interface module 408 may facilitate communication between the medical software tools platform system 400 and an image stream processing system utilized to process an image stream acquired by a surgical camera or the like. Through the communication, the image stream processing system interface module 408 may transmit control data to an image stream processing system, or receive an image stream from a surgical camera as processed by the image stream processing system. The image stream processing system interface module 408 may include various data interfaces, including wired or wireless network interfaces and serial communication interfaces.

Figure 5:
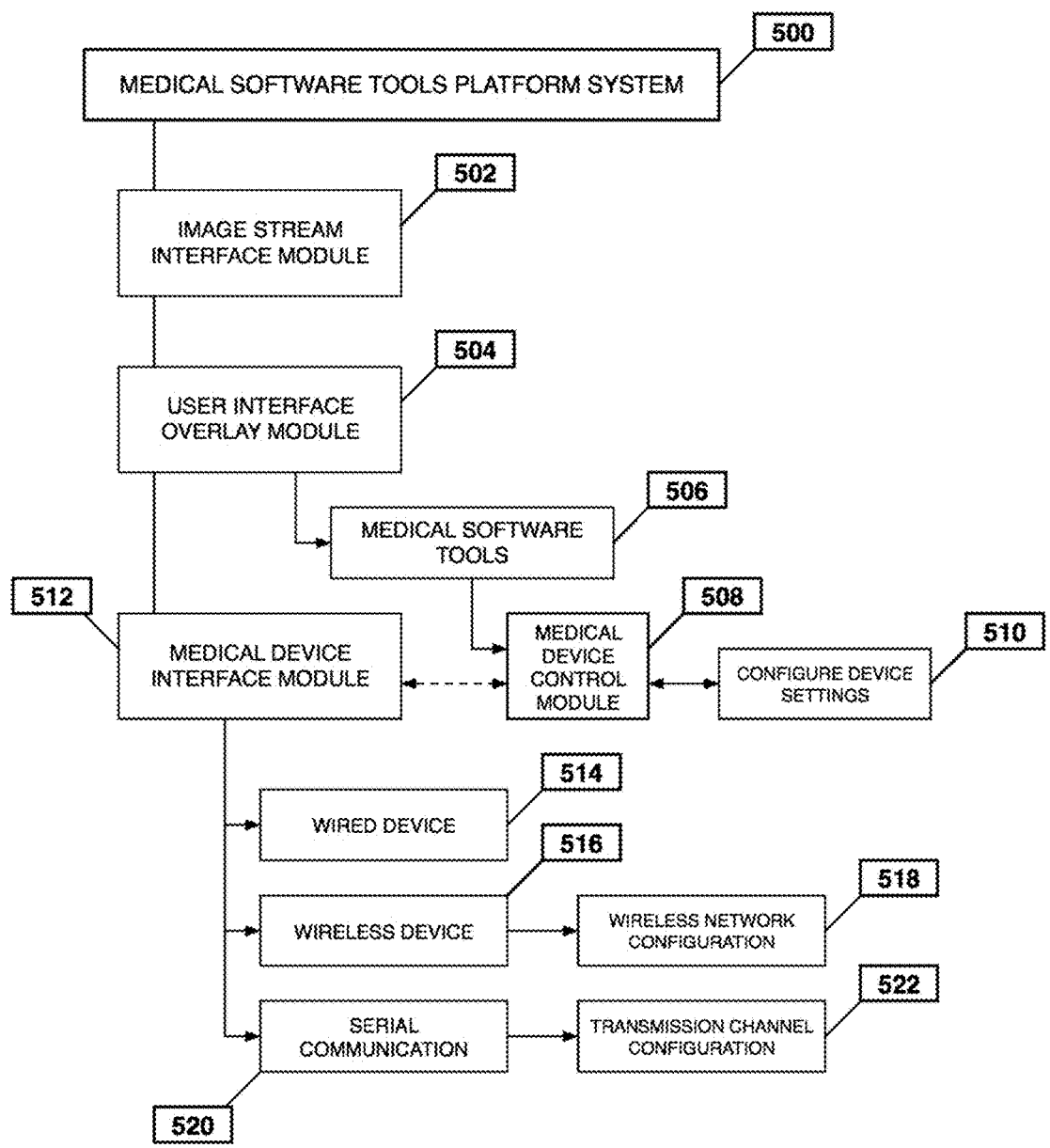
FIG. 5 is a block diagram illustrating the medical device control module within the medical tools software platform.

FIG. 5 is a block diagram illustrating the medical device control module within the medical software tools platform. In accordance with the preferred embodiment of the present invention, the medical software tools platform system 500 uses an image stream interface module 502 that may receive an image stream from an image stream processing system. The image stream received through the image stream interface module 502 is utilized within the user interface overlay module 504, which may include one or more graphical user interface (GUI) elements presented over the image stream received through the image stream interface module 502. For some embodiments, the user interface comprises a bottom toolbar configured to be presented over the image stream, and configured to provide access to various medical software tools 506.

The medical device control module 508 may facilitate control of one or more various medical devices utilized in an operating room. In particular, the medical device control module 508 may control operation of a medical device or configure settings 510 of the medical device. Medical devices controllable by way of the medical device control module 508 may include those that are network-enabled using a standard network interface.

The medical device interface module 512 may facilitate communication between the medical software tools platform system 500, one or more of the medical software tools 506, and one or more various medical devices utilized in an operating room. For instance, the medical device interface module 512 may enable the medical device control module 508 to control one or more medical devices utilized during a surgical procedure. Accordingly, the medical device interface module 512 may transmit control data to a medical device, or receive information collected by a medical device. The medical device interface module 512 may include various data interfaces, including but not limited to: wired devices 514; wireless devices 516 configured by wireless network interfaces 518; and serial communication 520 configured by transmission channel 522 interfaces.

Figure 6:
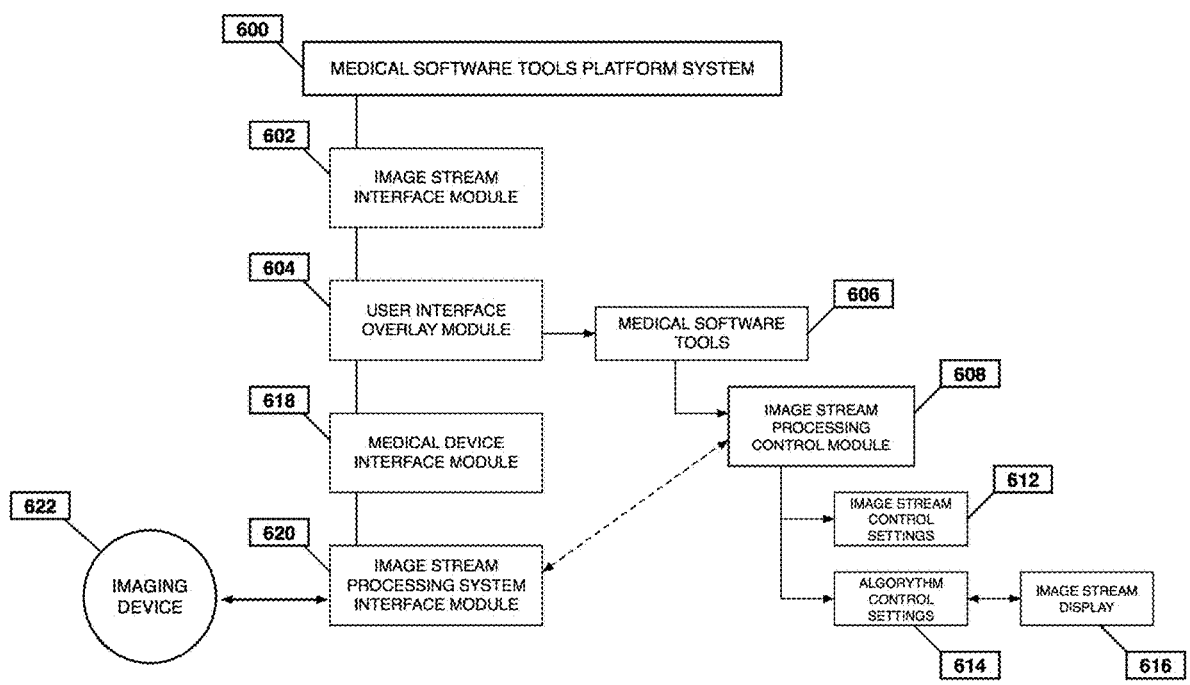
FIG. 6 is a block diagram illustrating image stream processing control module within the medical tools software platform.

FIG. 6 is a block diagram illustrating image stream processing control module within the medical tools software platform. In accordance with the preferred embodiment of the present invention, the medical software tools platform system 600 may receive an image stream from an image stream processing system. The image stream received through the image stream interface module 602 is utilized within the user interface overlay module 604, which may include one or more graphical user interface (GUI) elements presented over the image stream received through the image stream interface module 602. The user interface overlay module 604 also communicates with the medical device interface module 618 to facilitate communication between the medical software tools platform system 600, and one or more of the medical software tools 606, such as the image stream processing control module 608.

For some embodiments, the user interface overlay module 604 comprises a bottom toolbar configured to be presented over the image stream, and configured to provide access to medical software tools 606 such as the image stream processing control module 608. The image stream processing control module 608 may facilitate control of an image stream processing system interface module 620 utilized in an operating room to process an image stream acquired by an imaging device 622. The image stream processing control module 608 allows the user to control image stream settings 612 transmitted via the image stream processing system interface module 620. Depending on the embodiment, the image stream processing control module 608 may determine which image stream processing algorithms 614 are applied to the image stream before it is presented on a video display 616.

Figure 7:
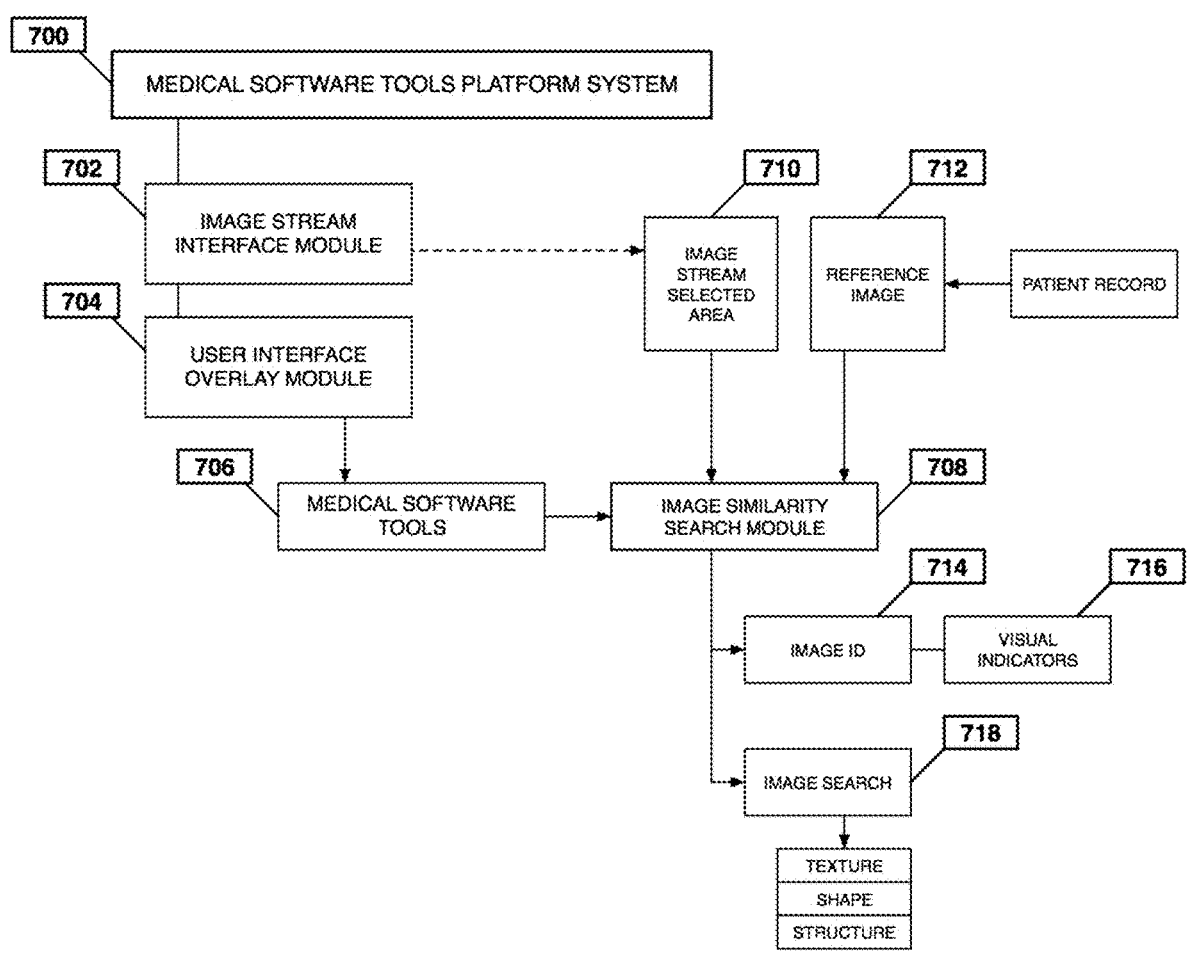
FIG. 7 is a block diagram illustrating image similarity search module within the medical software tools platform.

FIG. 7 is a block diagram illustrating the image similarity search module within the medical tools software platform. In accordance with the preferred embodiment of the present invention, the medical software tools platform system 700 may receive an image stream from an image stream processing system through the image stream interface module 702. A specific area of the overall image stream can be selected 710 or a reference image 712 taken from a patient record can be utilized within the user interface overlay module 704, which may include one or more graphical user interface (GUI) elements presented over the image stream received through the image stream interface module 702. The user interface overlay module 704 enables communication between the medical software tools platform system 700, and one or more of the medical software tools 706, such as the image similarity search module 708.

The image similarity search module 708 may facilitate identification or search of a texture, shape, structure, or size in content of an image stream based on selected area of the image stream 710 or a reference image 712. The image similarity search module may include adjustable sensitivity settings for the identification or search operations 718. The reference image 712 used for the identification 714 or search operation 718 may be one obtained from a patient's medical record, or one previously captured from the image stream 710. During identification operations 714, the image similarity search module 708 may augment the image stream with visual indicators 716 (e.g., hatching, call outs, lead lines, arrows, highlighting, or labels) to indicate similar texture, shape, structure, or size.

Figure 8:
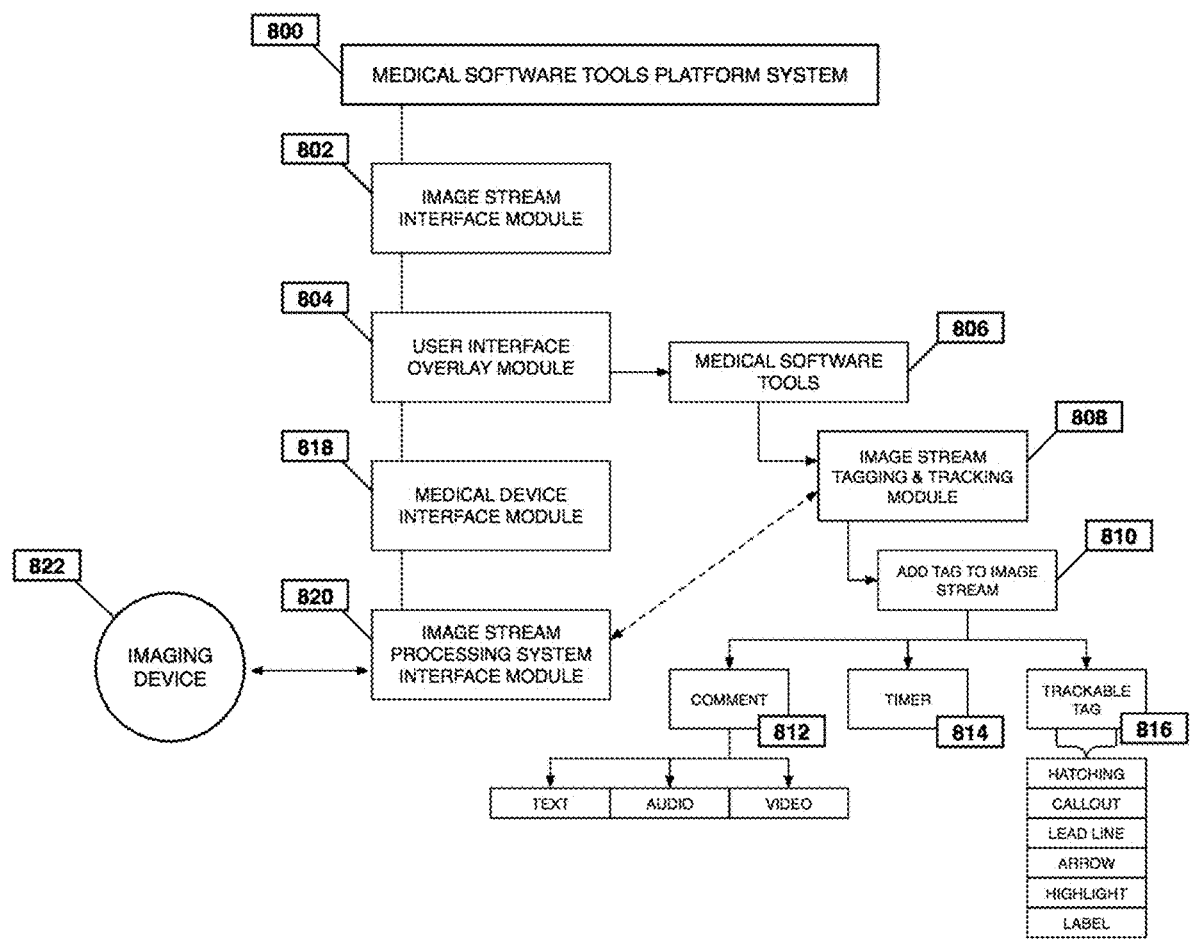
FIG. 8 is a block diagram illustrating image stream tagging and tracking module within the medical software tools platform.

FIG. 8 is a block diagram illustrating the image stream tagging and tracking module within the medical tools software platform. In accordance with the preferred embodiment of the present invention, the medical software tools platform system 800 may receive an image stream from an image stream processing system. The image stream received through the image stream interface module 802 is utilized within the user interface overlay module 804, which may include one or more graphical user interface (GUI) elements presented over the image stream received through the image stream interface module 802. The user interface overlay module 804 also communicates with the medical device interface module 818 to facilitate communication between the medical software tools platform system 800, and one or more of the medical software tools 806, such as the image stream tagging and tracking module 808.

For some embodiments, the user interface overlay module 804 comprises a bottom toolbar configured to be presented over the image stream, and configured to provide access to medical software tools 806 such as the image stream tagging and tracking module 808. The image stream tagging and tracking module 808 may communicate with an image stream processing system interface module 820 utilized in an operating room to process an image stream acquired by an imaging device 822. The medical device interface module 818 may facilitate communication between the medical software tools platform system 800, one or more of the medical software tools 806, such as the image stream tagging and tracking module 808

The image stream tagging and tracking module 808 may facilitate placement of one or more visual tags 810 with respect to an anatomical structure or tissue presented in an image stream received through the image stream interface module. Once placed, the visual tag 810 may be presented over the anatomical structure or tissue through the user interface provided by the user interface overlay module 804. The image stream tagging and tracking module 808 may also facilitate tag tracking such that the visual tags continue to maintain their position with respect to the anatomical structure or tissue (or some other specimen) when positioning between the surgical camera and the anatomical structure or tissue changes. In this way, the visual tags can be "sticky" with respect to the anatomical structure or tissue and correctly indicate their original placement with respect to the anatomical structure or tissue. Where the anatomical structure or tissue goes out of view (e.g., goes off screen), the image stream tagging and tracking module may restore visual tag positioning when the anatomical structure or tissue returns into view by adding trackable tags 816.

Depending on the embodiment, a visual tag may be associated with textual, audio, or video commentary 812, or associated with a timer 814 (e.g., clock, countdown timer, stop-watch, alarm) added through a component of the medical software tools platform system 800 (e.g., the timer module). Depending on the embodiment, the visual tags can be trackable 816 and may comprise hatching, call outs, lead lines, arrows, highlighting, or labels. In some instances, a tag can serve as a bookmark to a location of interest for a medical procedure. For example, as a bookmark a tag may assist a user (e.g., a surgeon) in visually revisiting locations of events that have occurred during a medical procedure, such as the location of a tissue biopsy or the insertion location of an object embedded in a patient's body (e.g., a sponge, clamp, or staple).

Figure 9:
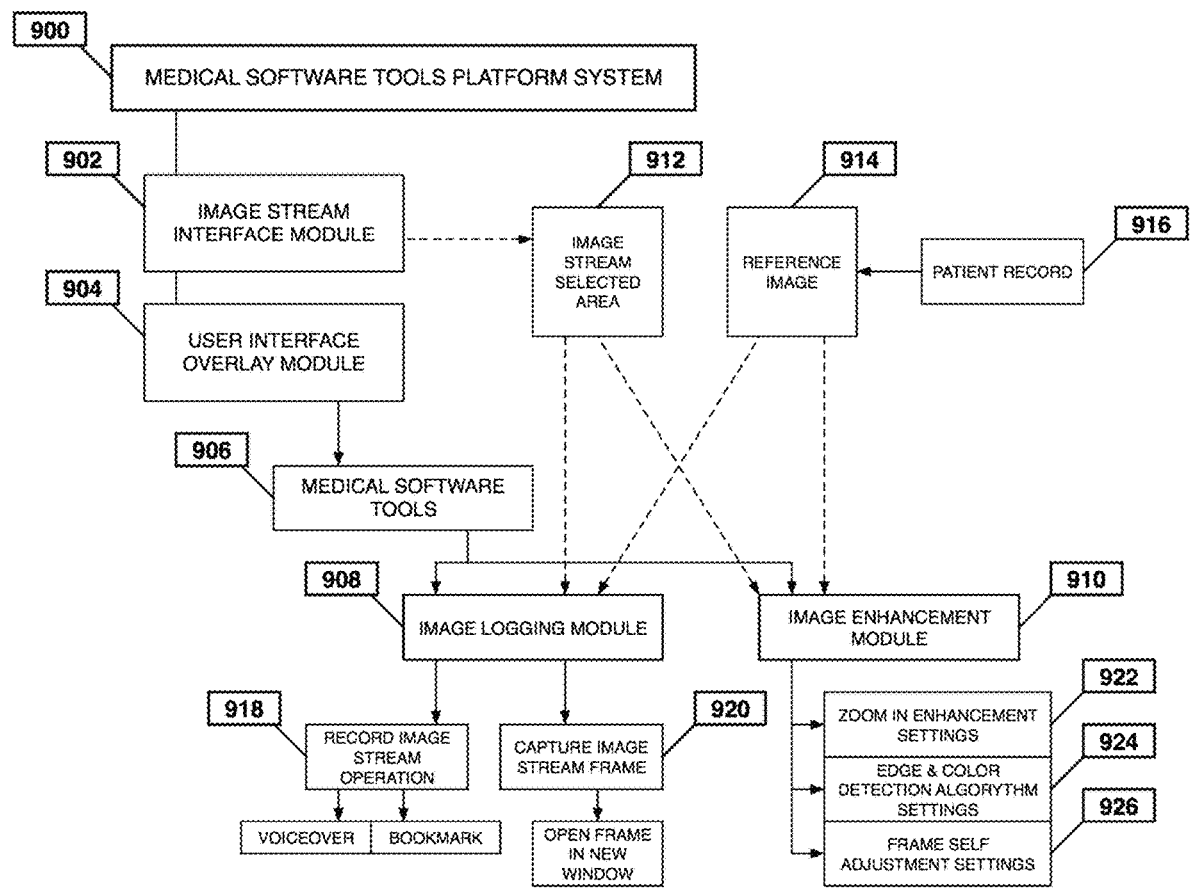
FIG. 9 is a block diagram illustrating the image logging and image enhancement modules within the medical software tools platform.

FIG. 9 is a block diagram illustrating the image logging and image enhancement modules within the medical tools software platform. In accordance with the preferred embodiment of the present invention, the medical software tools platform system 900 may receive an image stream from an image stream processing system through the image stream interface module 902. A specific area of the overall image stream can be selected 912 or a reference image 914 taken from a patient record 916 can be utilized within the user interface overlay module 904, which may include one or more graphical user interface (GUI) elements presented over the image stream received through the image stream interface module 902. the user interface overlay module 904 enables communication between the medical software tools platform system 900, and one or more of the medical software tools 906, such as the image logging module 908, and image enhancement module 910.

The image logging module 908 may facilitate recording operations with respect to an image stream. According to some embodiments, the image logging module enables recording of the image stream 918 with a voice-over or a bookmark, or capturing of frames from an image stream 920 (e.g., drag-and-drop a frame from the image stream to a window). Some or all of the functionality of the image logging module may be facilitated through an image stream recording system or an image stream processing system.

The image enhancement module 910 may facilitate improving the resolution of an image stream using information from several different frames to create new, higher resolution frames. The image enhancement module 910 may further facilitate: zooming to enlarge selected regions of the image stream 922; configure the algorithm settings for image edge and color detection 924; and configure frame self-adjustment settings 926. The image enhancement module 910 may utilize an image stream processing system in implementing some or all the image enhancements it applies.

Figure 10:
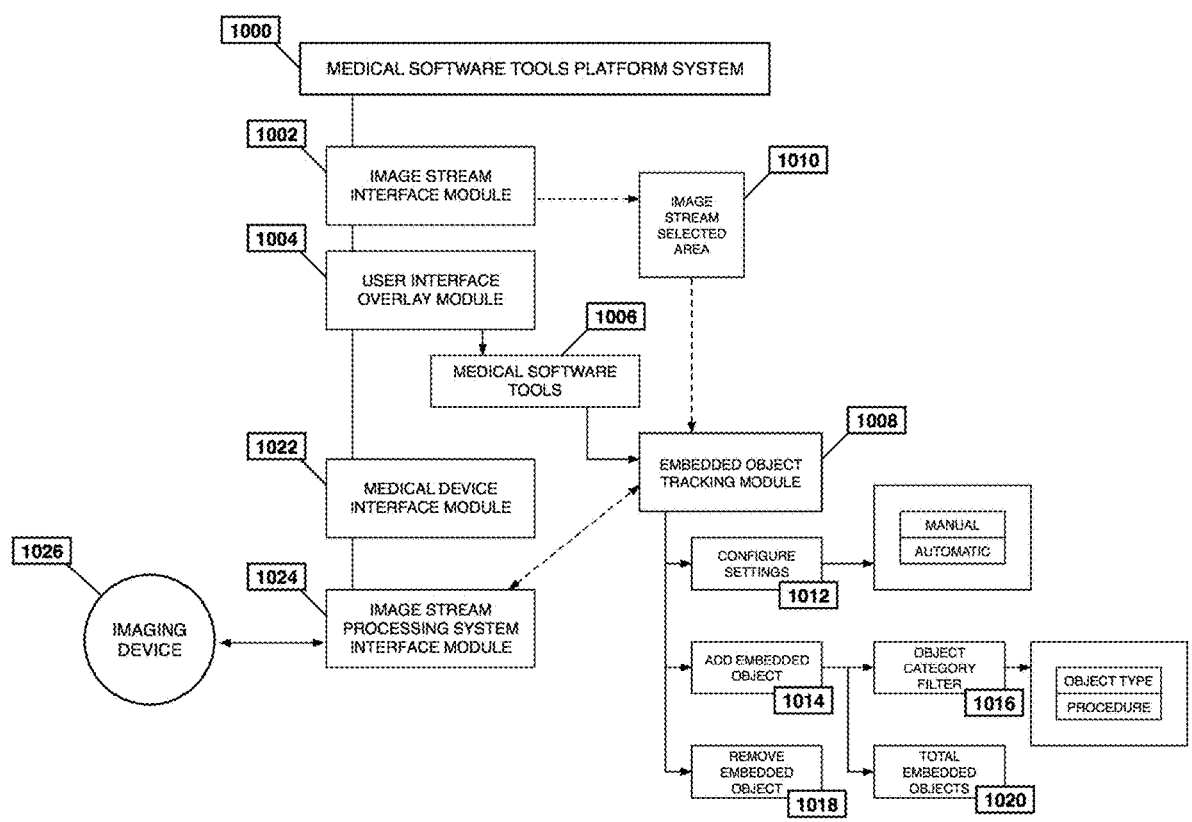
FIG. 10 is a block diagram illustrating embedded object tracking module within the medical software tools platform.

FIG. 10 is a block diagram illustrating embedded object tracking module within the medical tools software platform. In accordance with the preferred embodiment of the present invention, the medical software tools platform system 1000 may receive an image stream from an image stream processing system through the image stream interface module 1002. A specific area of the overall image stream can be selected 1010 and utilized within the user interface overlay module 1004, which may include one or more graphical user interface (GUI) elements presented over the image stream received through the image stream interface module 1002. the user interface overlay module 1004 enables communication between the medical software tools platform system 1000, and one or more of the medical software tools 1006, such as the embedded object tracking module 1008. The embedded object tracking module 1008 may communicate with an image stream processing system interface module 1024 utilized in an operating room to process an image stream acquired by an imaging device 1026. The medical device interface module 1022 may facilitate communication between the medical software tools platform system 1000, one or more of the medical software tools 1006, such as the embedded object tracking module 1008.

The embedded-object tracking module 1008 may enable a user (e.g., surgeon) to track objects embedded in a patient's body (hereafter, "embedded objects") during a medical procedure, such a sponges, clamps, and the like. For example, the embedded-object tracking module 1008 may enable tracking of embedded objects by allowing a user to maintain a count of embedded objects used during a medical procedure 1020. According to some embodiments, the embedded object tracking module 1008 maintains the count by adding to the count 1014 when objects are embedded in a patient's body, and subtracting from the count when embedded objects are removed from within the patient's body 1018. The count may be maintained manually by way of user input (e.g., by a surgeon's input to a touch screen display), or automatically by way of a process (e.g., imaging process) configured to automatically 1012 to detect the addition or removal of embedded objects. For some embodiments, the count of embedded objects is maintained according to categories 1016, such as object type (e.g., a separate count for sponges, and a separate count for clamps) or association to a procedural step.

The embedded-object tracking module 1008 may also track embedded objects by maintaining a listing of the objects embedded into a patient's body during a medical procedure 1020. For example, the embedded-object tracking module may maintain the list of embedded objects by a user indicating, or a process automatically detecting, when a particular embedded object has been added 1014 to a patient's body or when the particular embedded object has been removed 1018 from the patient's body. In addition, the listing of objects may include the count of embedded objects 1020 as described herein. The embedded object tracking module 1008 may further track embedded objects by remembering the location of embedded objects in a patient's body. Once remembered, the embedded-object tracking module may include visual indicators with respect to such embedded objects when they appear on a video display, such as highlighting or indicator lines.

Figure 11:
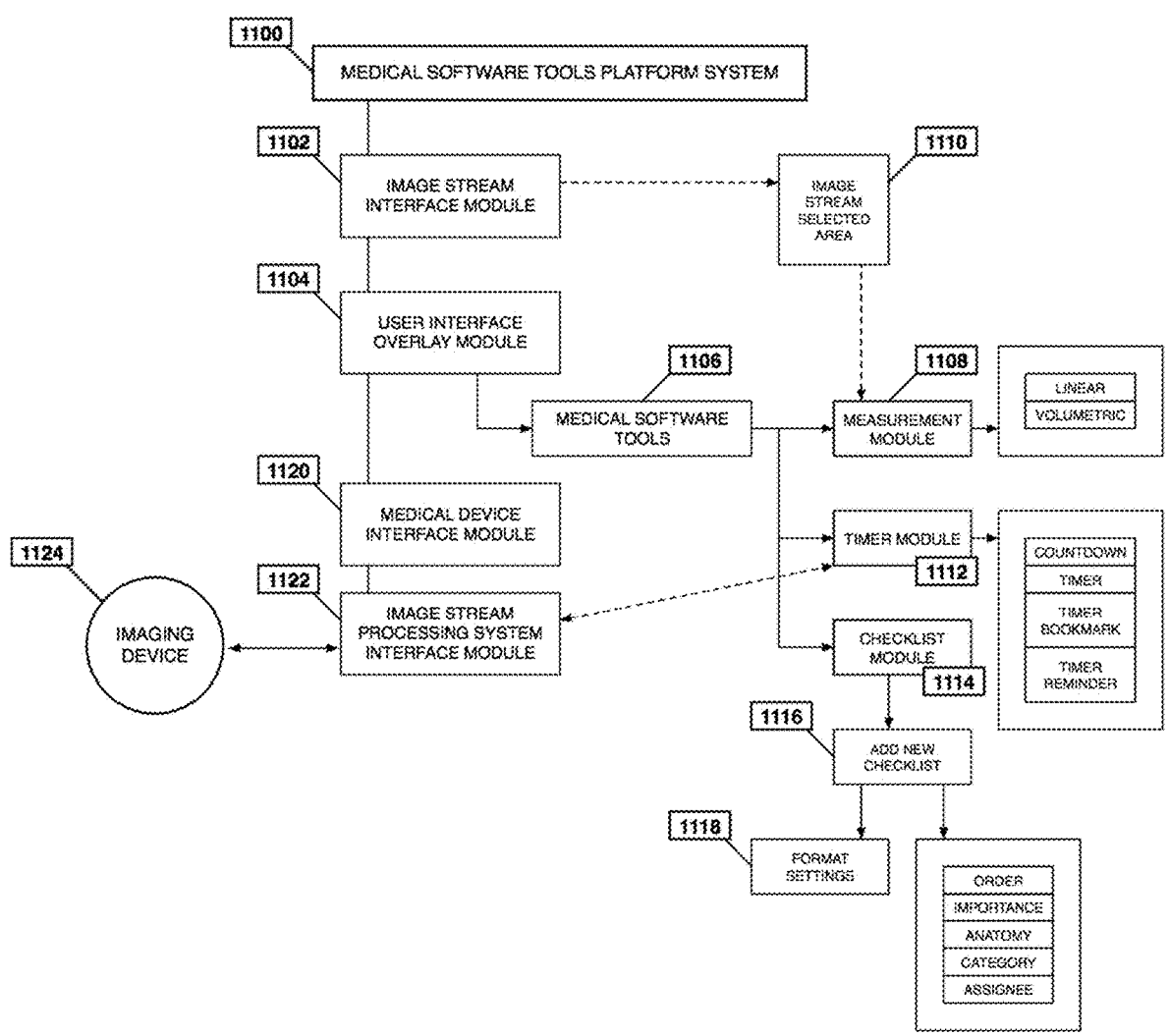
FIG. 11 is a block diagram illustrating the measurement, timer and checklist modules within the medical software tools platform.

FIG. 11 is a block diagram illustrating the measurement, timer and checklist modules within the medical tools software platform. In accordance with the preferred embodiment of the present invention, the medical software tools platform system 1100 may receive an image stream from an image stream processing system through the image stream interface module 1102. A specific area of the overall image stream can be selected 1110 and utilized within the user interface overlay module 1104, which may include one or more graphical user interface (GUI) elements presented over the image stream received through the image stream interface module 1102. the user interface overlay module 1104 enables communication between the medical software tools platform system 1100, and one or more of the medical software tools 1106, such as the measurement module 1008, timer module 1112, and checklist module 1114.

The medical device interface module 1120 may facilitate communication between the medical software tools platform system 1100, and one or more of the medical software tools 1106, such as the measurement module 1008, timer module 1112, and checklist module 1114. The measurement module 1108 may facilitate measurement of one or more anatomical structures or tissue presented in the content of an image stream received through the image stream interface module 1102. Depending on the embodiment, the measurement module 1108 may enable a user (e.g., surgeon) to select a region 1110 in the image stream and determine a measurement based on the selected region. The measurement may include linear measurements (e.g., width, height, length) and volumetric measurements of an anatomical structure or tissue delineated by the selected region.

The timer module 1112 may facilitate the addition of one or more countdown timers, clocks, stop-watches, alarms, or the like, that can be added and displayed over the image stream through the user interface provided by the user inter face overlay module 1104. For example, the timer module may allow a user (e.g., surgeon) to add a countdown timer in association with a surgical step (e.g., clamping an artery). For example, a countdown timer may be associated with a specific blood vessel that must be temporarily clamped during surgery but must be opened within a small window of time. A user may be able to select from a list of pre-defined countdown timers, which may have been pre-defined by the user. A clock when added may be used as a time bookmark during surgical procedures. The timer module 1112 may communicate with an image stream processing system interface module 1122 utilized in an operating room to process an image stream acquired by an imaging device 1124.

The checklist module 1114 may enable a user (e.g., surgeon) to add and maintain a checklist in connection with a medical procedure 1116. For example, the checklist module 1114 may provide a list of checklist items for a medical procedure. Each checklist item may indicate whether a step of the medical procedure has been completed or has yet to be completed. The checklist module 1114 may allow a user to present the check list in different ways using the checklist module formatting settings 1118. For instance, the checklist items may be organized and presented according to their procedural order, their importance, their relation to a patient's anatomy, their category, or their assigned individual (e.g., checklist item is the nurse's responsibility versus the surgeon's responsibility). In another example, the checklist items may be presented in using a different visual structures, such as a tree structure or a scrolling list.

Figure 12:
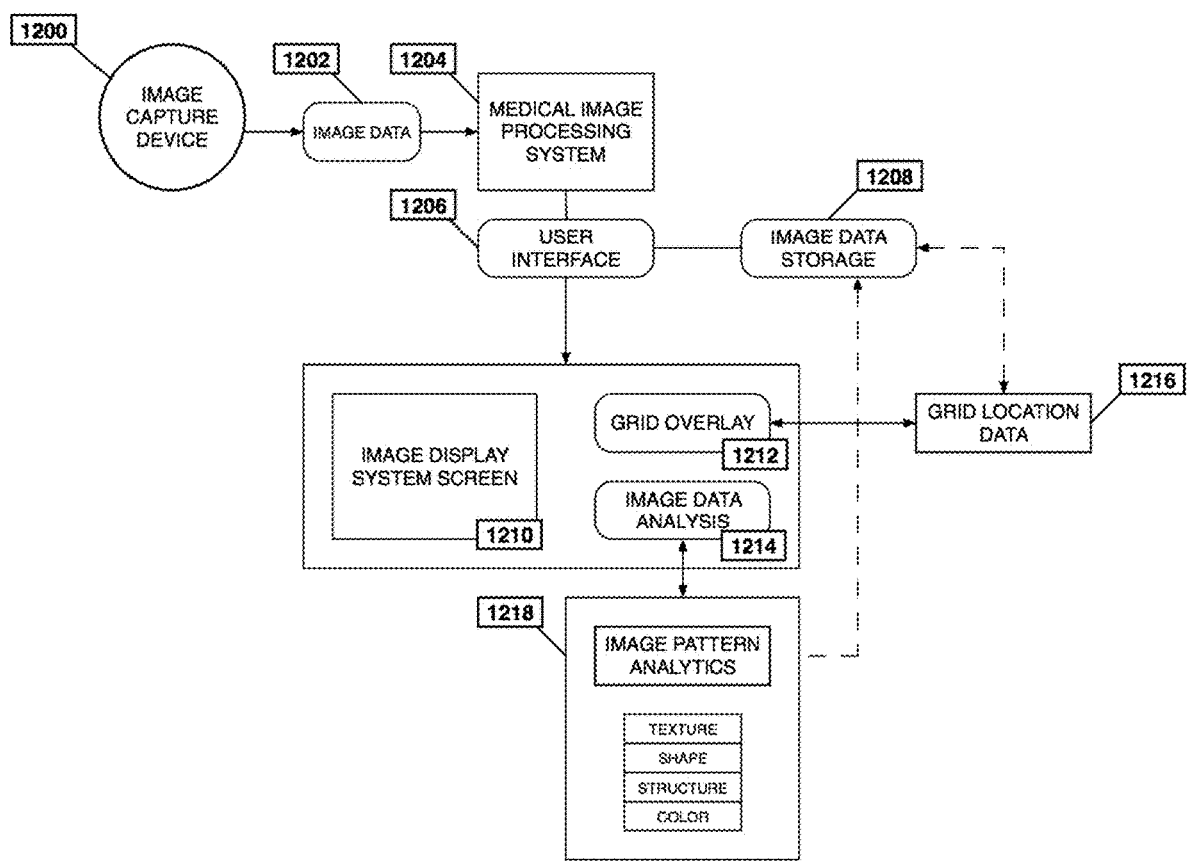
FIG. 12 is a block diagram illustrating the grid overlay module within the medical software tools platform.

FIG. 12 is a block diagram illustrating the grid overlay module within the medical tools software platform. In accordance with the preferred embodiment of the present invention, image data 1202 from an image stream acquired by an image capture device 1200, such as a surgical camera, is transmitted to a medical image processing system 1204. The user interface 1206 module within the medical image processing system 1204 may include one or more graphical user interface (GUI) elements presented over the image data 1202 stream on an image display system screen 1210. The user interface 1206 also displays a grid overlay 1212 and image data analysis 1214 information with the image display system screen 1210. Using the image data analysis 1214 function, the user interface 1206 presents the image data stream 1202 with enhancements using image pattern analytics 1218 that include but are not limited to: differences in tissue color, temperature and surface texture; automatically configured optical identification of tissue variations; and spectral signature measurements.

Through the medical image processing system 1204 user interface 1206, the image data 1202 is stored 1208, and the grid overlay 1212 that has been formatted by the user is also stored as easily searchable and retrievable grid location data 1216. The grid overlay too 1212 functions to identify the location of biopsy samples, and uses image data analysis 1214 to suggest areas of tissue to sample. The image display system screen 1210 uses selectable color bands to histogram analysis and the overall visual grid location selected from the image data stream 1202 is stored as synchronized video metadata.

Figure 13:
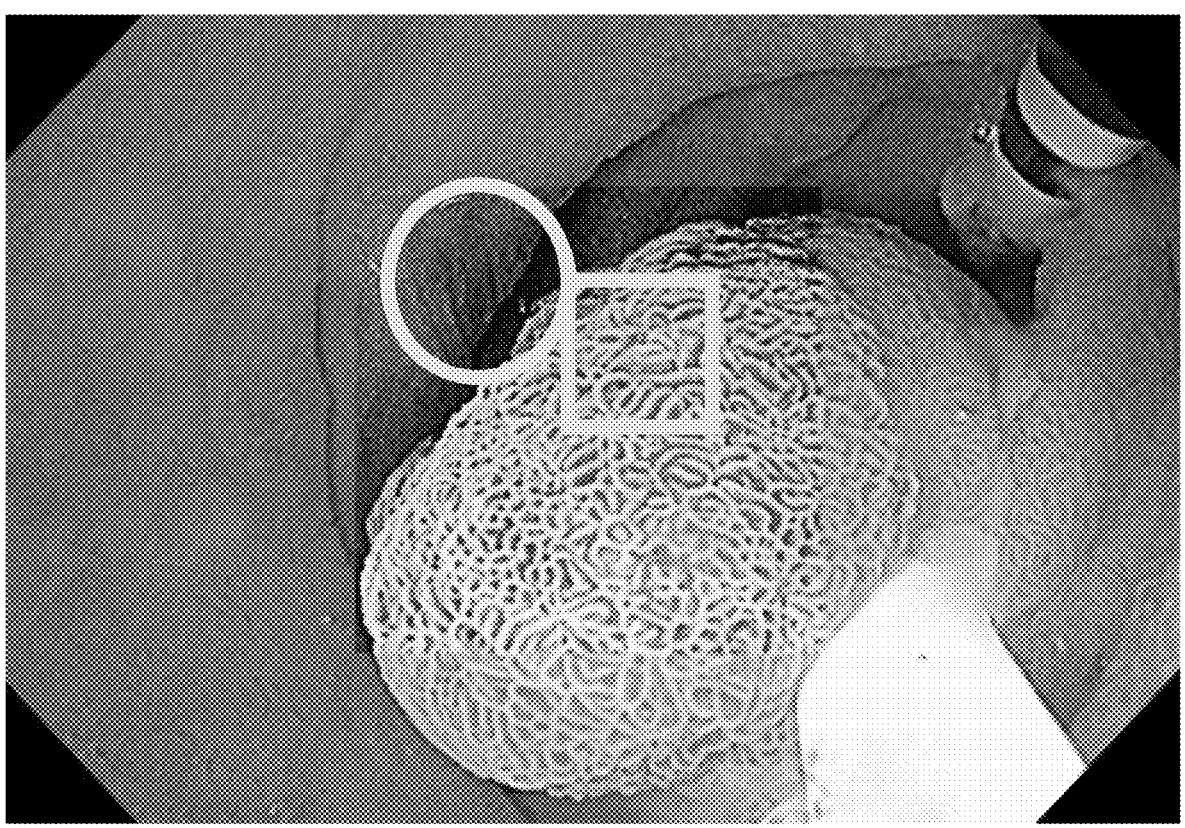
FIG. 13 is a rendering of the image annotation function applied to a surgical image.

FIG. 13 is a rendering of the image annotation function used in a surgical image. In accordance with the preferred embodiment of the present invention, the image annotation function describes a method to identify abnormal areas of tissue during laparoscopy to assist with biopsy site selection. The proposed method creates a map of areas (islands) with similar spectral characteristics. The image from an endoscope consists of an array of pixels consisting of values of color or luminance. A computer can determine areas (islands) of relative similarity by first finding spectral peaks in the image array by ranking occurrences of color or luminance values present in a range using a histogram. Once the peaks (dots) are collected, different algorithms will describe areas (islands) of similarity by connecting the dots using virtual non-intersecting lines according to a choice of rules (closest neighbor, equidistant points between, others) to Tessellate the area under study. Varying the histogram range and selection of color/luminance components to build an array of counts of similar tissue islands can provide input to an algorithm that visually highlights areas in the image for analysis or biopsy.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for medical software tools, comprising:
    an image stream from a surgical camera, utilizing a medical image processing system with a graphics user interface;
    a user interface overlay display configured to provide a user interface overlay adapted for presentation over the image stream;
    a set of medical software tools configured to provide a medical software tool through the user interface, the set of medical software tool being configured to perform an operation with respect to the image stream and provide an output adapted to be presented over the image stream;
    an image stream processing algorithm employed by said medical image processing system with said graphics user interface for said image stream from said surgical camera, using a color and structural analysis of said surgery related images gathered during said operation; and
    a medical image processing input and output interface for gathering, storing and viewing surgery related images obtained in connection with endoscopic surgical procedures utilizing a histogram relying on said color and structural analysis from said image processing algorithm.

2. The system according to claim 1, wherein said medical software tools utilize a core and graphics processing unit, and an integrated circuit such as a field-programmable gate array, to process and categorize raw data and utilize algorithms to process pixel convolutions deriving from said surgical camera and a medical archive.

3. The system according to claim 1, wherein the procedure and operation-specific actions comprise of applying said visual tag over said image stream with a two-dimensional and three-dimensional view of anatomical structure, tissue, or bodily interior presented in said image stream.

4. The system according to claim 2, wherein an image overlay is presented over said image stream, via said graphics processing unit supporting said timer modules and said checklist modules, with said visual tag comprising of the duration of time elapsed, timers, a histogram presenting selectable color bands and predefined settings for comparison of regions of similarity from said image stream and stored media for said image overlay.

5. A method for a set of medical software tools, comprising:
streaming an image on an image stream interface module, producing an image stream from a surgical camera;
overlaying presentations over the image stream;
providing a medical software tool through the user interface by way of a medical software tools module;
performing an operation with respect to the image stream;
providing an output and visual tag adapted to be presented over the image stream;
collecting, storing, and assessing surgery related images acquired in connection with endoscopic surgical procedures, wherein said process of collecting said surgery related images entails a color and luminance analysis of pixel values of said surgery related images;
visually processing the collected surgical and medical imagery and data; and
inputting said visually processed surgical and medical imagery and data into an algorithm to visually highlight an area of said surgical and medical imagery and data.

6. The method according to claim 5, wherein the procedure and operation-specific actions comprise of applying said visual tag over said image stream with a two-dimensional and three-dimensional view of anatomical structure, tissue, or bodily interior presented in said image stream.

7. The method according to claim 5, wherein said image stream derives from a plurality of input and output devices, including a medical ultrasound device, and imaging devices and configures to a switching matrix on said medical software tools module in communication with said plurality of input and output devices.

8. The method according to claim 5, wherein the operation comprises of timing said operation with respect to the visual tag and presenting a histogram throughout the duration of said operation to display the spectral characteristics of said operation.

9. The method according to claim 5, wherein said medical software tool utilizes a core and graphics processing unit, and an integrated circuit such as a field-programmable gate array for algorithms to process pixel convolutions to categorize raw data deriving from said surgical camera and medical archives.

10. The method according to claim 7, wherein said medical software tool engages in systemic pre-processing, enhancing, storing, and transporting of raw surgical and video data through the use of said switching matrix in communication with said plurality of input and output devices.

11. The method according to claim 10, wherein said medical software tool utilizes an anatomical reference image for a procedure including those in a patient's record to track monitor changes in a medical archive, and convert said anatomical reference image into a three-dimensional format through an image processing module.

* * * * *